United States Patent [19]

Pelosi, Jr. et al.

[11] 4,439,608

[45] Mar. 27, 1984

[54] 2-[2-(5-PHENYLFURFURYLAMINO)ETHYL]-PYRIDINES

[75] Inventors: Stanford S. Pelosi, Jr.; Chia-Nien Yu, both of Norwich, N.Y.

[73] Assignee: Norwich Eaton Pharmaceuticals, Inc., Norwich, N.Y.

[21] Appl. No.: 384,871

[22] Filed: Jun. 4, 1982

[51] Int. Cl.³ ............................................ C07D 405/12
[52] U.S. Cl. .................................................... 546/283
[58] Field of Search ........................................ 546/283

[56] References Cited

U.S. PATENT DOCUMENTS 4,145,348  3/1979  Pelosi, Jr. et al. ................... 546/283

Primary Examiner—John M. Ford
Assistant Examiner—Bernard Dentz
Attorney, Agent, or Firm—Anthony J. Franze

[57] ABSTRACT

2-[2-(5-Phenylfurfurylamino)ethyl]pyridines are useful as antihypertensive agents.

3 Claims, No Drawings

2-[2-(5-PHENYLFURFURYLAMINO)ETHYL]PYRIDINES

This invention is concerned with chemical compounds and particularly with 2-[2-(5-phenylfurfurylamino)ethyl]pyridines of the formula:

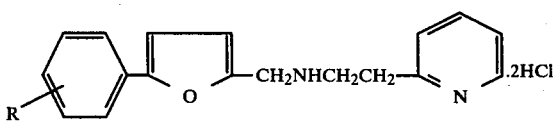

where R represents 4-nitro or 3,4-dimethoxy and a method for their preparation.

These compounds possess pharmacologic activity. In particular they exhibit antihypertensive activity when administered intraperitoneally to warm-blooded animals. Thus when administered intraperitoneally in a pharmaceutically acceptable solvent, such as saline, at a dose of 50 mg/kg to unanesthetized spontaneously hypertensive rats, reductions in the arterial blood pressure are elicited.

The compounds of this invention are readily prepared. Currently it is preferred to react the 5-phenyl-2-furaldehyde with 2-(2-aminoethyl)pyridine in a solvent such as methanol followed by treatment with sodium borohydride.

In order that this invention may be readily available to and understood by those skilled in the art, the following examples are supplied.

EXAMPLE I

2-[2-[5-(4-Nitrophenyl)furfurylamino]ethyl]pyridine Dihydrochloride

A mixture of 54 g (0.25 mole) of 5-(4-nitrophenyl)-2-furaldehyde and 30.5 g (0.25 mole) of 2-(2-aminoethyl)pyridine in 300 ml of methanol was heated under reflux for 2½ hours. The resulting solution was cooled to 25°, and 9.5 g (0.25 mole) of sodium borohydride was added in portions over 1 hour at 25°–30°. The solution was heated under reflux for 15 min, and the solvent was removed on a rotary evaporator. The residual solid was partitioned between water and chloroform. The chloroform layer (400 ml) was separated, dried over MgSO$_4$, and concentrated on a rotary evaporator to give 81 g of a reddish brown, oily residue which solidified on standing. The residual solid was dissolved in 400 ml of absolute methanol and treated with 200 ml of absolute methanol saturated with hydrogen chloride with cooling in ice. The yellow solid which was deposited was collected by filtration using a rubber dam and dried in a vacuum oven at oil pump pressure at 100° C. for 8 hr to give 86 g (87%) of product. Two additional recrystallizations from absolute methanol gave an analytical sample, m.p. 173°–177°.

Anal. Calcd. for $C_{18}H_{17}N_3O_3 \cdot 2HCl$: C, 54.56; H, 4.83; N, 10.60 Found: C, 54.94; H, 4.94; N, 10.57

EXAMPLE II

2-[2-[5-(3,4-Dimethoxyphenyl)furfurylamino]ethyl]pyridine Dihydrochloride Tetartohydrate A mixture of 17 g (0.14 mole) of 2-(2-aminoethyl)pyridine, 32.4 g (0.14 mole) of 5-(3,4-dimethoxyphenyl)-2-furaldehyde in 500 ml of anhydrous methanol was heated under reflux for 4 hr. Evaporation of methanol gave a viscous red liquid. This red liquid was then placed in 300 ml of fresh anhydrous methanol in a 1 liter 3-necked flask fitted with a stirrer, a thermometer and a condenser. Powdered sodium borohydride (5.3 g, 0.14 mole) was added portionwise such that the temperature of the reaction mixture never exceeded 35°. The addition was completed in about 40 min. The mixture was allowed to stir for an additional hour at ambient temperature and then was heated at reflux for ½ hour. The solvent was evaporated under reduced pressure to give an orange-red residual solid. The solid was partitioned between chloroform and water. The chloroform layer was dried over MgSO$_4$ and then concentrated at reduced pressure to a viscous liquid. Trituration of this viscous liquid with 150 ml of ethanolic HCl gave a dark solid. The solid was collected, washed with SDA-32 and air dried. The yield was 38.6 g (66%). Two recrystallizations from SDA-32 and Darco afforded 19.6 g of product, m.p 154°–156°.

Anal. Calcd. for $C_{20}H_{22}N_2O_3 \cdot 2HCl \cdot \tfrac{1}{4}H_2O$: C, 57.77; H, 5.94; N, 6.74 Found: C, 57.52; H, 6.18; N, 6.58

What is claimed is:

1. A compound of the formula:

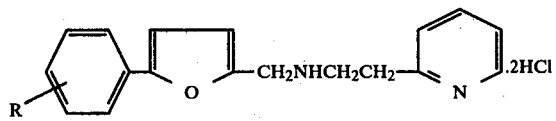

wherein R represents 4-nitro or 3,4-dimethoxy.

2. The compound 2-[2-[5-(4-nitrophenyl)furfurylamino]ethyl]pyridine dihydrochloride.

3. The compound 2-[2-[5-(3,4-dimethoxyphenyl)furfurylamino]ethyl]pyridine dihydrochloride tetartohydrate.

* * * * *